United States Patent
Zhang et al.

(10) Patent No.: US 9,933,452 B2
(45) Date of Patent: Apr. 3, 2018

(54) SIT-TO-STAND TRANSFER DETECTION

(75) Inventors: Wei Zhang, Eindhoven (NL); Heribert Baldus, Aachen (DE); Stephan Schlumbohm, Frankfurt (DE)

(73) Assignee: Koninklijke Philips N.V., Eindhoven (NL)

( * ) Notice: Subject to any disclaimer, the term of this patent is extended or adjusted under 35 U.S.C. 154(b) by 803 days.

(21) Appl. No.: 14/126,576

(22) PCT Filed: Jun. 19, 2012

(86) PCT No.: PCT/IB2012/053083
§ 371 (c)(1),
(2), (4) Date: Dec. 16, 2013

(87) PCT Pub. No.: WO2013/001411
PCT Pub. Date: Jan. 3, 2013

(65) Prior Publication Data
US 2014/0114604 A1   Apr. 24, 2014

(30) Foreign Application Priority Data
Jun. 28, 2011 (EP) .................................. 11171700

(51) Int. Cl.
*G01P 15/00* (2006.01)
*A61B 5/11* (2006.01)
*A61B 5/00* (2006.01)

(52) U.S. Cl.
CPC ............ *G01P 15/00* (2013.01); *A61B 5/1116* (2013.01); *A61B 5/7282* (2013.01); *A61B 5/6822* (2013.01); *A61B 2562/0219* (2013.01)

(58) Field of Classification Search
CPC ...... G01P 15/00; A61B 5/1116; A61B 5/7282; A61B 5/6822; A61B 2562/0219
(Continued)

(56) References Cited

U.S. PATENT DOCUMENTS 6,152,890 A    11/2000  Kupfer et al.
2004/0015103 A1*  1/2004  Aminian ............... A61B 5/1116
                                                600/595

(Continued)

FOREIGN PATENT DOCUMENTS

EP          1195139       4/2002
JP        2003296782 A    10/2003

(Continued)

OTHER PUBLICATIONS

K.M. Kerr, et al, "Analysis of the Sit-Stand-Sit Movement Cycle in Normal Subjects", Clinical Biomechanics, vol. 12, No. 4, Jun. 1997, pp. 236-245.

*Primary Examiner* — David M Gray
*Assistant Examiner* — Geoffrey T Evans

(57) ABSTRACT

There is provided a method for identifying a sit-to-stand transfer in measurements of the movement of a user, the method comprising obtaining measurements of the vertical acceleration experienced by the user during movement; obtaining measurements indicating changes in height of a part of the user during movement; processing the measurements of the vertical acceleration to identify candidate movements corresponding to a sit-to-stand transfer by the user; and determining an identified candidate movement as a sit-to-stand transfer where the identified candidate movement coincides with an increase in height. A corresponding apparatus and computer program product are also provided.

20 Claims, 5 Drawing Sheets

(58) Field of Classification Search
USPC .......................................................... 702/141
See application file for complete search history.

(56) References Cited

U.S. PATENT DOCUMENTS

| | | | | |
|---|---|---|---|---|
| 2006/0251334 A1* | 11/2006 | Oba | .................... | A61B 5/1122 |
| | | | | 382/275 |
| 2009/0254003 A1 | 10/2009 | Buckman | | |
| 2009/0322540 A1 | 12/2009 | Richardson et al. | | |
| 2010/0191697 A1 | 7/2010 | Fukumoto et al. | | |
| 2010/0204615 A1 | 8/2010 | Kyle et al. | | |
| 2010/0256531 A1* | 10/2010 | Nishibayashi | ........ | A61B 5/1118 |
| | | | | 600/595 |
| 2011/0172951 A1 | 7/2011 | Schlumbohm | | |
| 2011/0178760 A1 | 7/2011 | Schlumbohm et al. | | |
| 2015/0302720 A1* | 10/2015 | Zhang | .................. | A61B 5/7246 |
| | | | | 340/573.7 |

FOREIGN PATENT DOCUMENTS

| | | | |
|---|---|---|---|
| JP | 2004275214 A | 10/2004 | |
| JP | 20090076419 A1 | 4/2009 | |
| JP | 2010207488 A | 9/2010 | |
| WO | WO2010035187 | 4/2010 | |

* cited by examiner

SIT-TO-STAND TRANSFER DETECTION

CROSS-REFERENCE TO PRIOR APPLICATIONS

This application is the U.S. National Phase application under 35 U.S.C. § 371 of International Application Serial No. PCT/IB2012/053083, filed on Jun. 19, 2012, which claims the benefit of European Application Serial No. 11171700.5, filed on Jun. 28, 2011. These applications are hereby incorporated by reference herein.

TECHNICAL FIELD OF THE INVENTION

The invention relates to a method and apparatus for identifying a sit-to-stand transfer movement by a user.

BACKGROUND TO THE INVENTION

Falls are one of the greatest health risk factors for elderly people. About one third of older people above the age of 65 fall at least once a year.

Many of these falls could be avoided by early identification of fall risk and the application of effective and targeted fall prevention programs.

Fall prevention trials based on strength and balance training (SBT) have shown that the risk of falling for elderly people can be reduced. Balance performance measures can be used as early indicators of fall risk, and also to measure the progress of fall prevention programs. The 'sit-to-stand' (STS) transfer has been identified as one important movement which can be used as a balance performance measure. Domain experts can compare the graph of the power generated during a sit-to-stand transfer for fall prevention with the ECG graph in cardiovascular disorders. In daily life, a person performs the STS transfer many times a day.

Conventionally, only clinical measurement systems (such as those including a force plate and an optical marker system) allow an accurate quantification of power during a sit-to-stand transfer. In these measurement systems, the force plate provides the vertical ground reaction force and the optical marker system provides a measure of displacement in three dimensions. The combination of both measurements is used to quantify the power during a sit-to-stand transfer.

These measurement systems have several drawbacks. Firstly, they are clinical equipment, which requires the user to attend a clinic. Preparing for and performing measurements is labor intensive (particularly if optical markers need to be attached to specific parts of the body). In addition, they only provide a snapshot of the user's balance performance, where, owing to the clinical setting, the user commonly performs above their average capability. Finally, the measurement systems involve a procedure which is quite cumbersome for the user.

WO 2010/035187 entitled "Power Measurement and Apparatus" discusses an apparatus for estimating the peak power used by a user in performing the vertical component of a movement, such as a sit-to-stand transfer, the apparatus comprising an accelerometer for attachment to a user and for measuring the acceleration experienced by a user; the apparatus further comprising a processor configured to receive the measurements of the acceleration from the accelerometer attached to the user; estimate the vertical accelerations from the received measurements; and estimate the power used from the vertical accelerations.

Existing activity monitoring technologies identify postures or movements by classifying a sequence of sensor data of tens of seconds or minutes in length. However, it is difficult to accurately detect a sit-to-stand transfer that is typically completed within 2 or 3 seconds.

Therefore, there is a need for a method and apparatus that can identify such a transfer from measurements of the movement of a user, so that the power used by the user in performing the movement can be calculated. There is also a need for a method and apparatus that can detect the onset and end of the transfer within a certain degree of accuracy in order for the power analysis to provide useful results.

SUMMARY OF THE INVENTION

According to a first aspect of the invention, there is provided a method for identifying a sit-to-stand transfer in measurements of the movement of a user, the method comprising obtaining measurements of the vertical acceleration experienced by the user during movement; obtaining measurements indicating changes in height of a part of the user during movement; processing the measurements of the vertical acceleration to identify candidate movements corresponding to a sit-to-stand transfer by the user; and determining an identified candidate movement as a sit-to-stand transfer where the identified candidate movement coincides with an increase in height.

According to a preferred embodiment, the step of processing the measurements of the vertical acceleration to identify candidate movements corresponding to a sit-to-stand transfer by the user comprises matching the measurements of the vertical acceleration to a predetermined acceleration profile for a sit-to-stand transfer.

Preferably, a candidate movement corresponding to a sit-to-stand transfer by the user is identified in the result of the step of matching where there is a peak, a first local minimum within a predetermined time period before the identified peak and a second local minimum within a predetermined time period after the identified peak.

Furthermore, the candidate movement corresponding to a sit-to-stand transfer by the user is preferably identified in the result of the step of matching where the peak has a magnitude in a predetermined range.

In a yet further preferred embodiment, a candidate movement corresponding to a sit-to-stand transfer is further identified where (i) the difference between the magnitude of the peak and the magnitude of the first local minimum is less than a first threshold value; (ii) the difference between the magnitude of the peak and the magnitude of the second local minimum is less than a second threshold value; and (iii) the magnitude of the second local minimum after the peak is less than the magnitude of the first local minimum.

In one embodiment, the step of determining an identified candidate movement as a sit-to-stand transfer comprises identifying a first sample in the measurements indicating changes in height that corresponds to a first sample, s1, in the result of the step of matching that is before the first local minimum that exceeds a first threshold value; identifying a second sample in the measurements indicating changes in height that corresponds to a first sample, s2, in the result of the step of matching that is after the second local minimum that exceeds a second threshold value; and determining the change in height of the part of the user from the identified first and second samples.

In that embodiment, the step of determining the change in height from the first and second samples comprises determining the average of the height of the part of the user over an evaluation window ending with the first sample; determining the average of the height of the part of the user over an evaluation window beginning with the second sample; and subtracting the two averages to give the change in height during the candidate sit-to-stand transfer.

In some embodiments, a more precise estimate of the start and end of the sit to stand transfer can be found by estimating the variation of the vertical acceleration; and determining the timing of the start and/or the end of the identified sit-to-stand transfer in the measurements of the vertical acceleration using the estimated variation.

Preferably, the step of determining the timing of the start of the identified sit-to-stand transfer comprises identifying a sample in the estimated variation that occurs before the first local minimum in the result of the step of matching and that that is below a third threshold value, the sample indicating the start of the identified sit-to-stand transfer.

Preferably, the step of determining the timing of the end of the identified sit-to-stand transfer comprises identifying a sample, s1, in the result of the step of matching that is before the first local minimum that exceeds a first threshold value; identifying a sample, s2, in the result of the step of matching that is after the second local minimum that exceeds a second threshold value; identifying the lowest value in the measurements of the vertical acceleration between s1 and s2; and identifying the first sample after the lowest value in the measurements of the vertical acceleration that exceeds a fifth threshold value, said sample indicating the end of the identified sit-to-stand transfer.

In a preferred embodiment, the step of obtaining measurements of the vertical acceleration experienced by the user during movement comprises obtaining three-dimensional measurements of the acceleration experienced by the user during movement; and processing the three-dimensional measurements to estimate the vertical acceleration experienced by the user.

According to a second aspect of the invention, there is provided a method of determining the power used during a sit-to-stand transfer by a user, the method comprising identifying a sit-to-stand transfer in measurements of the movement of a user according to the method described above; and processing the measurements of the vertical acceleration to determine an estimate of the power used during the sit-to-stand transfer.

According to a third aspect of the invention, there is provided a method of determining a risk of falling for a user, the method comprising determining the power used during a sit-to-stand transfer by a user as described above; and determining a risk of falling for the user from the determined power.

According to a fourth aspect of the invention, there is provided a computer program product, comprising computer program code that, when executed on a computer or processor, causes the computer or processor to identify a sit-to-stand transfer in measurements of the movement of a user as described above. Further computer program products are provided that cause a computer or processor to execute a method of determining the power used during a sit-to-stand transfer by a user and a method of determining a risk of falling for a user as described above.

According to a fifth aspect of the invention, there is provided an apparatus for identifying a sit-to-stand transfer in measurements of the movement of a user, the apparatus comprising a processor for processing measurements of vertical acceleration experienced by a user during movement to identify candidate movements corresponding to a sit-to-stand transfer by the user, and to determine an identified candidate movement as a sit-to-stand transfer where the identified candidate movement coincides with a measured increase in height.

According to a preferred embodiment, the processor is configured to identify candidate movements corresponding to a sit-to-stand transfer by the user by matching the measurements of the vertical acceleration to a predetermined acceleration profile for a sit-to-stand transfer.

Preferably, the processor is configured to identify a candidate movement corresponding to a sit-to-stand transfer by the user in the result of the matching where there is a peak, a first local minimum within a predetermined time period before the identified peak and a second local minimum within a predetermined time period after the identified peak.

Preferably, the processor is configured to identify a candidate movement corresponding to a sit-to-stand transfer by the user in the result of the matching where the peak has a magnitude in a predetermined range.

In a yet further preferred embodiment, the processor is further configured to identify a candidate movement corresponding to a sit-to-stand transfer where (i) the difference between the magnitude of the peak and the magnitude of the first local minimum is less than a first threshold value; (ii) the difference between the magnitude of the peak and the magnitude of the second local minimum is less than a second threshold value; and (iii) the magnitude of the second local minimum after the peak is less than the magnitude of the first local minimum.

In one embodiment, the processor is configured to determine an identified candidate movement as a sit-to-stand transfer by identifying a first sample in the measurements indicating changes in height that corresponds to a first sample, s1, in the result of the step of matching that is before the first local minimum that exceeds a first threshold value; identifying a second sample in the measurements indicating changes in height that corresponds to a first sample, s2, in the result of the step of matching that is after the second local minimum that exceeds a second threshold value; and determining the change in height of the part of the user from the identified first and second samples.

In that embodiment, the processor is configured to determine the change in height from the first and second samples by determining the average of the height of the part of the user over an evaluation window ending with the first sample; determining the average of the height of the part of the user over an evaluation window beginning with the second sample; and subtracting the two averages to give the change in height during the candidate sit-to-stand transfer.

In some embodiments, a more precise estimate of the start and end of the sit to stand transfer can be found where the processor is configured to estimate the variation of the vertical acceleration; and determine the timing of the start and/or the end of the identified sit-to-stand transfer in the measurements of the vertical acceleration using the estimated variation.

Preferably, the processor is configured to determine the timing of the start of the identified sit-to-stand transfer by identifying a sample in the estimated variation that occurs before the first local minimum in the result of the matching and that that is below a third threshold value, the sample indicating the start of the identified sit-to-stand transfer.

Preferably, the processor is configured to determine the timing of the end of the identified sit-to-stand transfer by identifying a sample, s1, in the result of the matching that is before the first local minimum that exceeds a first threshold value; identifying a sample, s2, in the result of the matching that is after the second local minimum that exceeds a second threshold value; identifying the lowest value in the measurements of the vertical acceleration between s1 and s2; and identifying the first sample after the lowest value in the measurements of the vertical acceleration that exceeds a fifth threshold value, said sample indicating the end of the identified sit-to-stand transfer.

In a preferred embodiment, the processor is configured to obtain three-dimensional measurements of the acceleration experienced by the user during movement; and to process the three-dimensional measurements to estimate the vertical acceleration experienced by the user.

According to a further embodiment, the apparatus is for determining the power used during a sit-to-stand transfer by a user, wherein the processor in the apparatus is further configured to identify a sit-to-stand transfer in measurements of the movement of a user; and to process the measurements of the vertical acceleration to determine an estimate of the power used during the sit-to-stand transfer.

According to a yet further embodiment, the apparatus is for determining a risk of falling for a user, wherein the processor in the apparatus is further configured to determine the power used during a sit-to-stand transfer by a user; and to determine a risk of falling for the user from the determined power.

BRIEF DESCRIPTION OF THE DRAWINGS

Embodiments of the invention will now be described, by way of example only, with reference to the following drawings, in which.

DETAILED DESCRIPTION OF THE PREFERRED EMBODIMENTS

Figure 1:
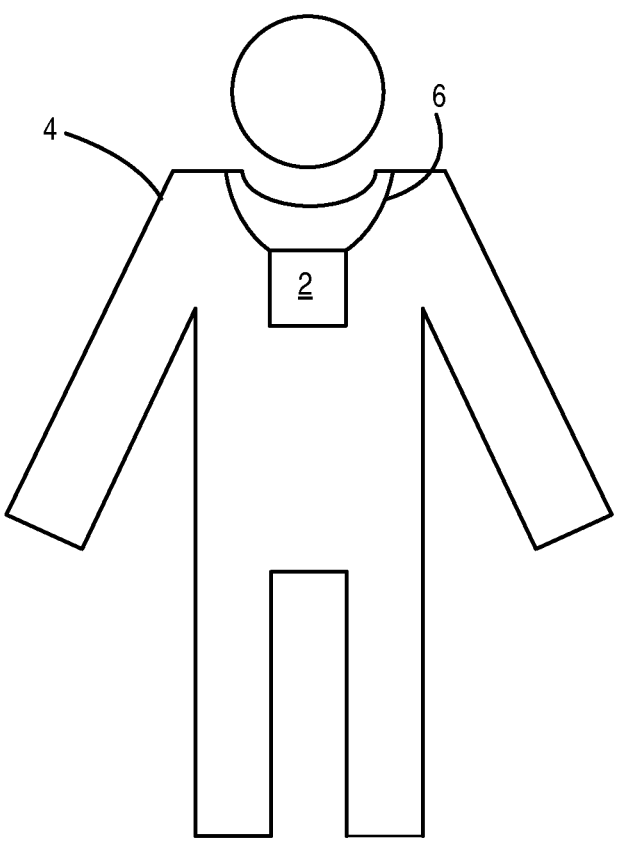
FIG. 1 shows a sensor unit in accordance with an embodiment of the invention attached to a user.

As shown in FIG. 1, the invention provides a sensor unit 2 that is to be worn by the user 4. In the illustrated embodiment, the sensor unit 2 is provided in the form of a pendant with a neck cord 6 for placement around the user's neck. Alternatively, the sensor unit 2 can be configured to be worn at or on a different part of the user's body, such as the trunk, pelvis or sternum, and will comprise a suitable arrangement for attaching the sensor unit 2 to that part of the body (for example a belt or a strap if the unit 2 is attached to the pelvis or sternum).

The sensor unit 2 is used to measure the movement of the user 4 and to process the measurements to determine when the user 4 has executed a sit-to-stand transfer. In preferred embodiments, the sensor unit 2 is also used to determine the power or strength used during the sit-to-stand transfer from the measurements of the movement of the body of the user 4. Alternatively, this processing can be performed in a base unit that is separate to the sensor unit 2 worn by the user 4 (not shown in FIG. 1).

Figure 2:
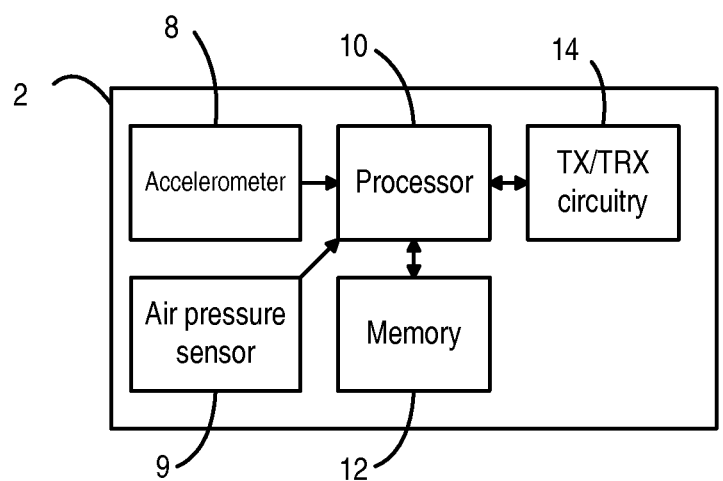
FIG. 2 is a block diagram of a sensor unit in accordance with an embodiment of the invention.

FIG. 2 shows a preferred embodiment of the sensor unit 2 in accordance with the invention. The sensor unit 2 comprises an accelerometer 8 that measures acceleration along three orthogonal axes and a sensor 9 that measures the altitude or height of the sensor unit 2 above the ground (or more particularly that measures changes in the altitude or height of the sensor unit 2 above the ground, or enables those changes to be measured). The sensor 9 for measuring the altitude or height of the sensor unit 2 can comprise, for example, an altimeter or air pressure sensor, although those skilled in the art will be aware of other types of sensors that can be used. The signals output by the accelerometer 8 and sensor 9 are provided to a processor 10 for analysis.

The sensor unit 2 also comprises a memory 12 and a transmitter or transceiver circuitry 14. The memory 12 is used for storing measurements from the accelerometer 8 and sensor 9, and for storing the results of the analysis by the processor 10. The transmitter or transceiver circuitry 14 is used for transmitting the results of the analysis to a remote (base) unit or a computer where they can be viewed or studied by the user or a healthcare provider.

In some embodiments, the accelerometer 8 is a microelectromechanical system (MEMS) accelerometer. The acceleration experienced by the accelerometer 8 can be sampled at a rate of 50 Hz, although it will be appreciated that many other sampling frequencies can be used. Where sensor 9 is an air pressure sensor or altimeter, the measurements of the height of the sensor unit 2 above the ground can be sampled at a frequency of around 1.8 Hz, although again it will be appreciated that other sampling frequencies can be used.

Depending on the particular type of sensor used for the sensor 9 for measuring height, the sensor 9 may output signals indicative of the height above the ground (or sea level in the case of an air pressure sensor), in which case the time series of height measurements can be analyzed by the processor 10 to determine the change in height from one measurement sample to the next (or over a predetermined number of measurement samples). Alternatively, the sensor 9 can directly output an indication of the change in height of the sensor unit 2 from the previous or an earlier specified measurement sample.

In an embodiment of the invention, the measurements collected by the accelerometer 8 and sensor 9 are analyzed by the processor 10 in the sensor device 2 to determine the occurrence of a sit-to-stand transfer, and optionally the power or peak power exerted by the user in performing the transfer. Alternatively, the measurements from the accelerometer 8 and sensor 9 could be transmitted to a base unit via the transmitter/transceiver circuitry 14, with the base unit analyzing the measurements to determine the occurrence of a sit-to-stand transfer. In either case, the processing can be performed in (near) real-time or the measurements from the accelerometer 8 and the sensor 9 can be stored in the memory 12 or the base unit for future processing (i.e. offline).

Figure 3:
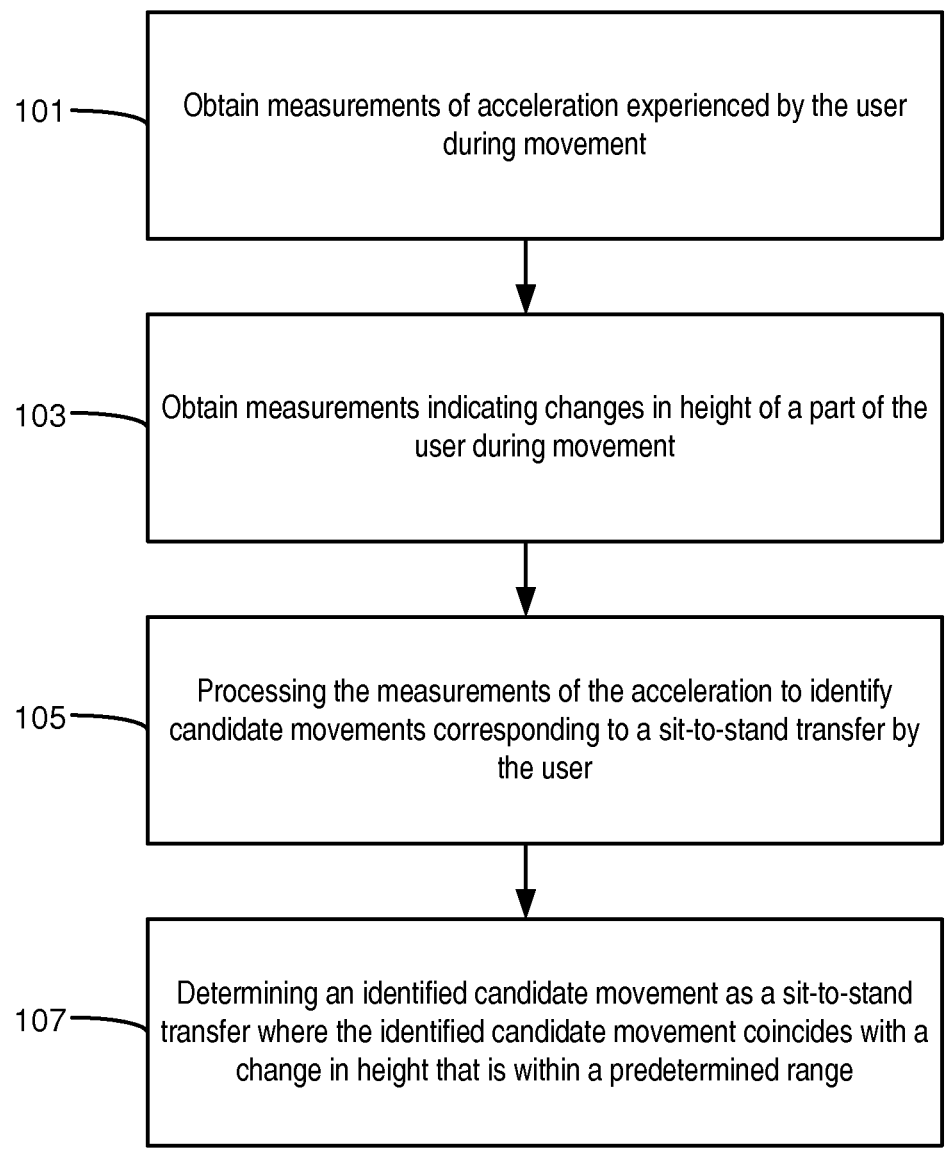
FIG. 3 is a flowchart illustrating a method for identifying a sit-to-stand transfer in measurements of the movement of a user.

FIG. 3 shows a flowchart illustrating the steps required to identify a sit-to-stand transfer in measurements of the movement of the user. Firstly (step 101), measurements of the acceleration experienced by the sensor unit 2 (and therefore the user 4, since the user is wearing the sensor unit 2) are obtained. Secondly (step 103), measurements of changes in the height of the sensor unit 2 (and therefore the part of the user 4 that the sensor unit 2 is attached to) above the ground are obtained. The measurements of the acceleration and height (or changes in height) are obtained over substantially the same period of time.

Next, in step 105, the measurements of the acceleration are processed to identify movements in the measurements that may correspond to a sit-to-stand transfer by the user 4. The parts of the accelerometer measurement (i.e. a sequence of measurement samples) that are identified in this step as possibly corresponding to a sit-to-stand transfer are termed 'candidate movements'.

In a preferred embodiment of the invention, the candidate movements are identified by matching the measurements of the acceleration to an acceleration profile that is expected to occur during a sit-to-stand transfer.

Figure 4:
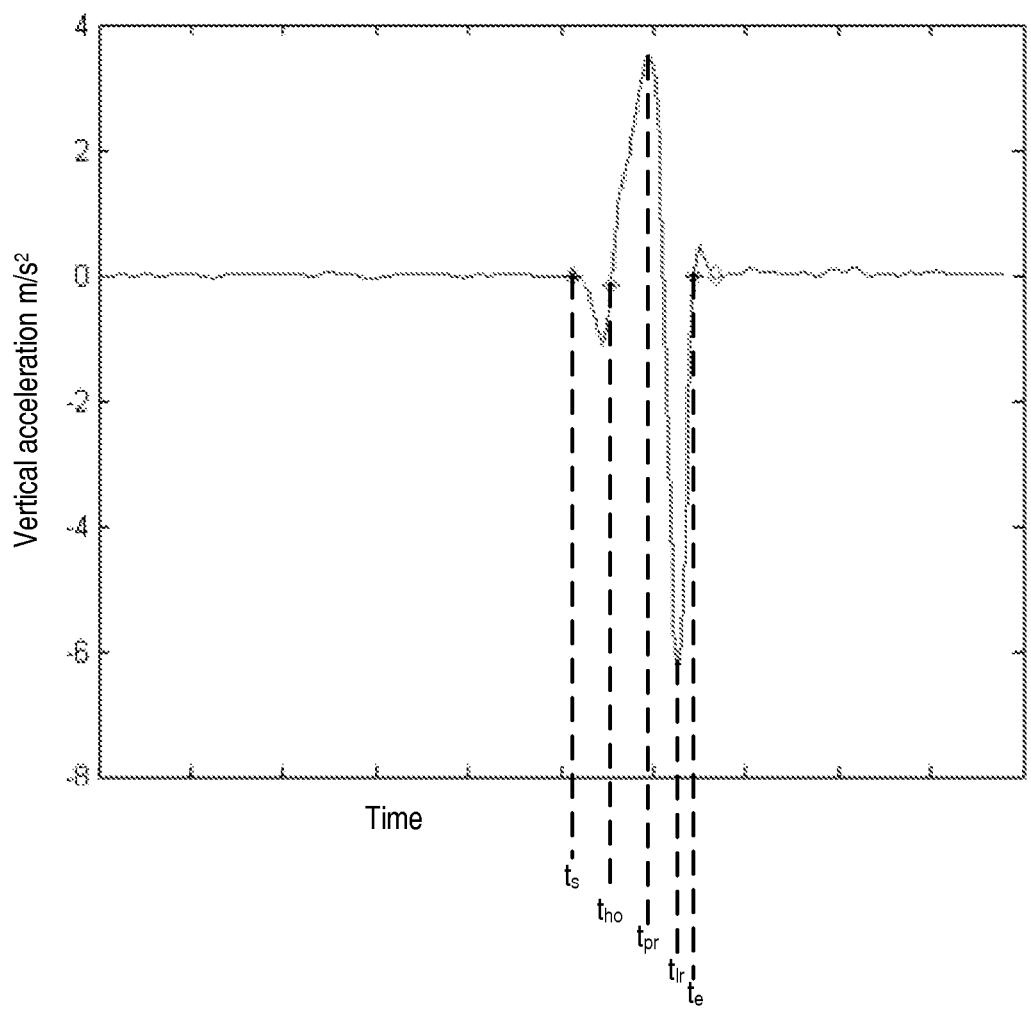
FIG. 4 is a graph illustrating an example of the variation in vertical acceleration during a sit-to-stand transfer.

The graph in FIG. 4 shows the acceleration measured in the vertical direction during a typical sit-to-stand motion. The user 4 starts from rest (i.e. the measured acceleration in the vertical direction is approximately 0) and the user begins to move at time $t_s$. The acceleration measured at this time is denoted $Acc_{vert\_s}$. There is typically a small minimum in the acceleration profile just after the user starts to move and before they rise off their chair. Subsequently, the user's hip leaves the means of support (i.e. chair) at time $t_{ho}$ ('ho' represents hip off), and the acceleration at this time is denoted $Acc_{vert\_ho}$. The acceleration in the vertical direction then increases to a peak (the peak reaction) denoted $Acc_{vert\_pr}$ at time $t_{pr}$. The peak reaction is followed by the lowest reaction which is a negative acceleration denoted $Acc_{vert\_lr}$ occurring at time $t_{lr}$. The end of the movement occurs at time $t_e$, with the acceleration denoted $Acc_{vert\_e}$.

Thus, in step 105 of the flowchart in FIG. 3, the candidate movements are identified by analyzing the accelerometer measurements to identify sequences of samples whose profile match or substantially match the profile shown in FIG. 4.

In step 107, the change in height occurring during each candidate movement is determined from the measurements obtained in step 103, and sit-to-stand transfers are determined to have occurred where any identified candidate movement coincides with a change in height that is within a predetermined range. The predetermined range encompasses the height changes expected to occur during a typical sit-to-stand transfer, which for example can correspond generally to length of the user's thigh. In this case, the lower bound for the range can be around 0.1 or 0.2 meters, for example, and the upper bound for the range can be set to a value of 0.6, 0.75, 0.8 or 1 meter, for example. It will be appreciated that the threshold can be personalized to the height or thigh length of the user and can also be set taking into account the resolution of the height or altitude measurements provided by the sensor 9.

It will also be appreciated that sit-to-stand transfers can alternatively be determined by comparing the change in height to a threshold value, with a sit-to-stand transfer being identified where the change in height exceeds the threshold value. In this case, the threshold can correspond to the lower bound for the predetermined range described above. However, this embodiment may result in a higher false positive identification rate than the range embodiment described above, since activities such as climbing the stairs may be identified as a sit-to-stand transfer (whereas this movement would be discarded as a possible sit-to-stand transfer by the upper bound of 0.6-1 meter in the range embodiment).

Figure 5:
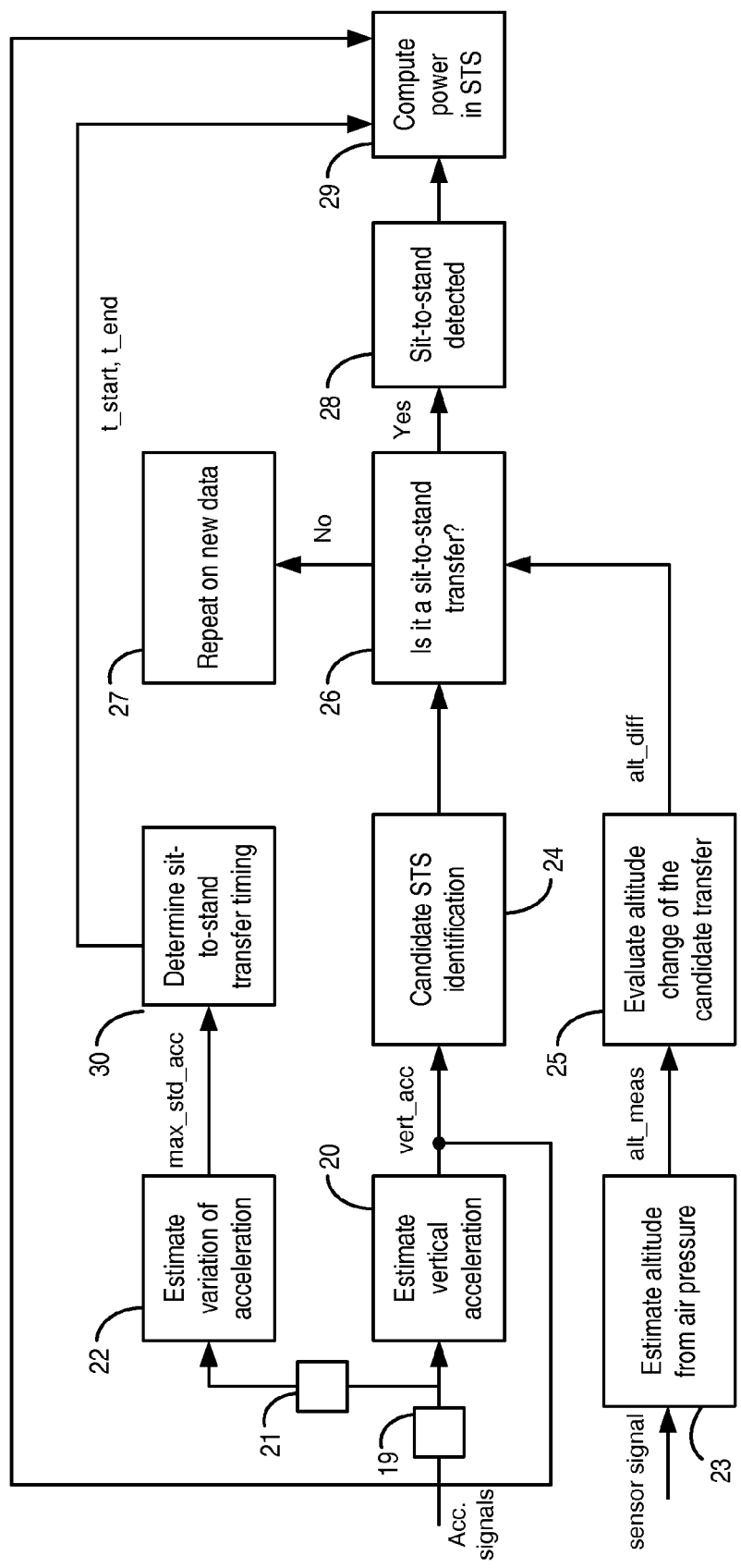
FIG. 5 is a block diagram illustrating an algorithm for detecting a sit-to-stand transfer.

A more detailed algorithm for detecting a sit-to-stand transfer in accordance with the invention and for determining the timing of the transfer is shown in FIG. 5. The algorithm takes as an input the three-dimensional acceleration signal measured by the accelerometer 8 (which comprises a separate signal for each of the three axes of the accelerometer 8) and an air pressure measurement from air pressure sensor 9.

The initial part of the algorithm, represented by blocks 19, 20, 21, 22 and 23, is a pre-processing stage in which the accelerometer and pressure sensor signals are processed for use in the subsequent analysis stages of the algorithm. Firstly, the 3D acceleration signals from the accelerometer 8 are low-pass filtered (block 19) to remove noise which could affect the accuracy of the subsequent processing. In one embodiment, a Butterworth low-pass filter with a cut-off frequency of 2 Hz is applied to the signals from each of the three axes of the accelerometer 8. Alternatively, it would be possible to apply different filter characteristics such as a Chebyshev low-pass filter or other types of filter known to those skilled in the art. It will also be appreciated that the cut-off frequency of 2 Hz could be varied dependent on the particular characteristics of the noise from the accelerometer 8.

As the orientation of the sensor unit 2 relative to the fixed reference frame (such as the Earth) in which the user 4 moves can change (particularly where the sensor unit 2 is in the form of a pendant), it is necessary to process the measurements from the accelerometer 8 to determine the vertical component of acceleration experienced by the sensor unit 2 (and therefore user 4) during the movement.

Therefore, the low-pass filtered 3D acceleration signals are input to block 20 that estimates the vertical acceleration. The vertical acceleration is denoted vert_acc.

One technique for estimating the vertical component of acceleration from a 3D accelerometer signal having an arbitrary orientation is described in WO 2010/035191, the content of which is hereby incorporated by reference. Briefly, according to that technique, the vertical component of acceleration is estimated from measurements of acceleration acting on an accelerometer, the accelerometer having an arbitrary orientation relative to the fixed reference frame, by (i) examining the signals from the accelerometer to identify the axis of the accelerometer having the highest component of acceleration, (ii) determining the orientation of the accelerometer by determining the angle between the acceleration acting on the accelerometer (this acceleration being assumed to be generally due to gravity) and the axis with the highest component of acceleration and (iii) using the estimated orientation of the accelerometer to determine the acceleration in the vertical direction from the measurements of acceleration.

Those skilled in the art will be aware of other techniques for estimating the vertical component of acceleration from the measurements from a 3D accelerometer. For example, the sensor unit 2 can include a gyroscope for providing a signal indicating the orientation of the sensor unit 2, and this signal can be used to derive the vertical component of acceleration.

FIG. 6(a) shows an exemplary signal representing the vertical acceleration obtained from measurements by a sensor unit 2 of a user performing a sit-to-stand transfer, walking for 3 meters and then sitting back down, which was repeated three times. It can be seen in FIG. 6(a) that there are three separate areas of activity represented in the signal.

Another stage of the pre-processing concerns the calculation of an estimate of the variation of acceleration. Firstly, a high pass filter 21 is applied to each of the low-pass filtered 3D acceleration signals in order to remove the DC component. In one embodiment, a Butterworth high-pass filter with a cut-off frequency of 0.5 Hz is used to remove the D.C.

component in the acceleration signals. It will be appreciated that another filter, for example a Chebyshev high-pass filter or other types of filter known to those skilled in the art could be used. It will also be appreciated that a different cut-off frequency to 0.5 Hz could be chosen.

After high-pass filtering, the variation of the acceleration is estimated in block 22. In a preferred embodiment, the standard deviation of each of the three components of the 3D acceleration signal is computed for a time t over a window of predetermined length (for example, one second, although it will be appreciated that another appropriately sized window could be used) and the maximum standard deviation out of the three axes is identified. The maximum standard deviation at time t is denoted max_std_acc and is given by equation 1 below.

$$\text{max\_std\_acc} = \max[\text{std}(\text{acc}\_i(t-0.5, t+0.5)), i=x,y,z] \quad (1)$$

Figure 6:
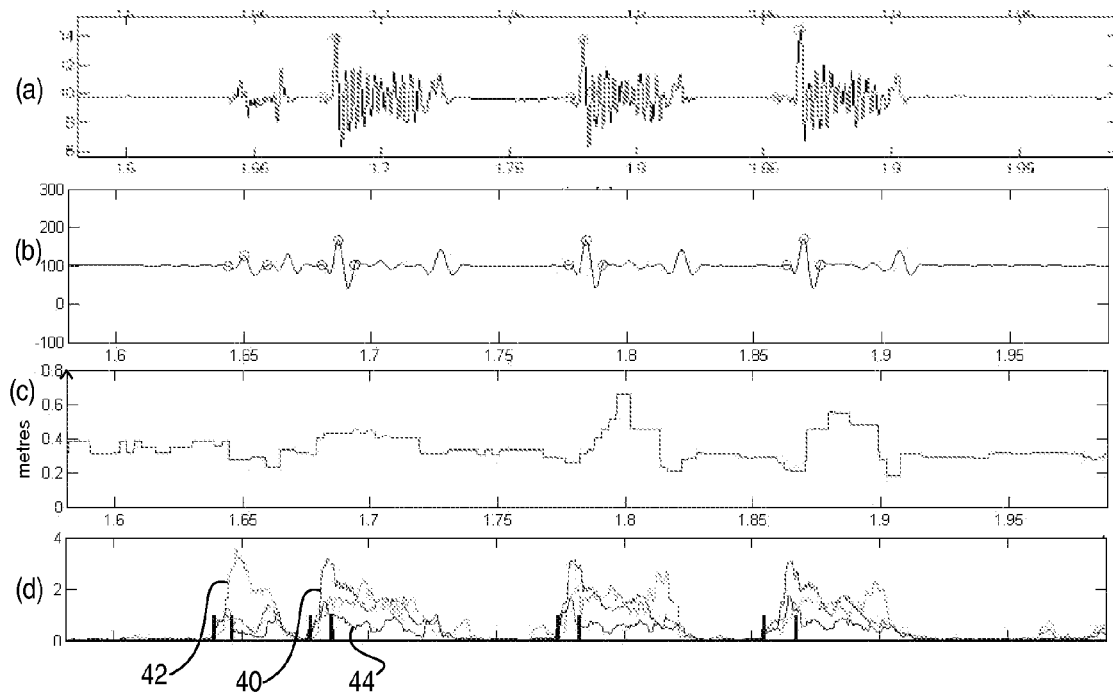
FIG. 6 shows the input signals to the algorithm and the signals obtained during some of the processing steps.

FIG. 6(*d*) shows the standard deviation calculated for each of the three axes of acceleration. In FIG. 6(*d*), line 40 corresponds to the x-axis accelerometer signal, line 42 corresponds to the y-axis accelerometer signal, and line 44 corresponds to the z-axis accelerometer signal.

A third pre-processing stage 23 estimates the altitude of the sensor unit 2 from the measurements from the air pressure sensor 9. As indicated above, the input to this stage 23 is the raw air pressure signal $p_t$ from the air pressure sensor 3. As mentioned previously, the air pressure can be sampled at a rate of 1.8 Hz (or in any case at a much lower sampling rate than the acceleration signals). Therefore, the air pressure signal $p_t$ is firstly upsampled to match the sampling rate (e.g. 50 Hz) of the acceleration signals (the upsampled pressure signal is denoted $p_t'$). The altitude at time t (denoted alt_t) can then be estimated from the air pressure sensor measurements using equation 2 below:

$$\text{alt}\_t = 44330 * (1 - p_t'/101325)^{0.19} \quad (2)$$

Equation (2) is derived from the air pressure to altitude conversion function shown in equation (3):

$$\text{alt}\_t = \frac{T_0}{L}\left(1 - \left(\frac{p}{p_0}\right)^{\frac{RL}{gM}}\right) \quad (3)$$

Where:

| Symbol | Quantity | Typical Value |
|---|---|---|
| alt_t | Altitude in meters | |
| p | Air pressure | |
| $p_0$ | Standard atmospheric pressure at sea level | 101325 kPa |
| L | Temperature lapse rate | 0.0065 Km$^{-1}$ |
| $T_0$ | Standard temperature at sea level | 288.15 K |
| g | Gravitational acceleration at Earth's surface | 9.80665 ms$^{-2}$ |
| M | Molar mass of dry air | 0.0289644 kg mol$^{-1}$ |
| R | Universal gas constant | 8.31447 J mol$^{-1}$ K$^{-1}$ |

The resulting altitude signal is then smoothed, preferably with a median filter having a predetermined length, for example of around 3 seconds. The filter is applied to the time series of estimated altitudes, resulting in a smoothed altitude signal alt_meas which is output from the altitude estimation stage 23, as shown in FIG. 6(*c*). In FIG. 6(*c*), the y-axis represents altitude in meters relative to sea level.

It will be appreciated that in alternative embodiments of the invention where a different type of altitude, height or change in height sensor is used, processing stage 23 may be adapted or omitted as appropriate.

Following the pre-processing of the input signals, various features are extracted in order to determine if a sit-to-stand transfer has occurred, and if so, the power of the user in performing the sit-to-stand transfer.

Two main stages of feature extraction are required in order to determine if a sit-to-stand transfer has occurred. The first stage 24 of the feature extraction executes step 105 of the flowchart in FIG. 3 and identifies the candidate movements in the vert_acc signal. In particular, block 24 matches the vert_acc signal to a predetermined pattern representing the vertical acceleration that is expected to occur during a sit-to-stand transfer.

In a preferred embodiment, the first stage 24 of the feature extraction applies a matched filter having an impulse response that approximates the vertical acceleration experienced during a sit-to-stand transfer to the vertical acceleration signal (vert_acc) output from the vertical acceleration estimation block 20. The output of the matched filter is a set of coefficients that indicate the match of the measurements to the pattern. Each coefficient represents the match of a number of consecutive measurement samples (covering a time period of the same length as the predetermined pattern) to the predetermined pattern. The higher the coefficient, the better the match of the measurements to the pattern (and therefore the greater the chance that a sit-to-stand transfer has occurred). The filtered signal is denoted vert_acc_matfilt and is shown in FIG. 6(*b*).

Figure 7:
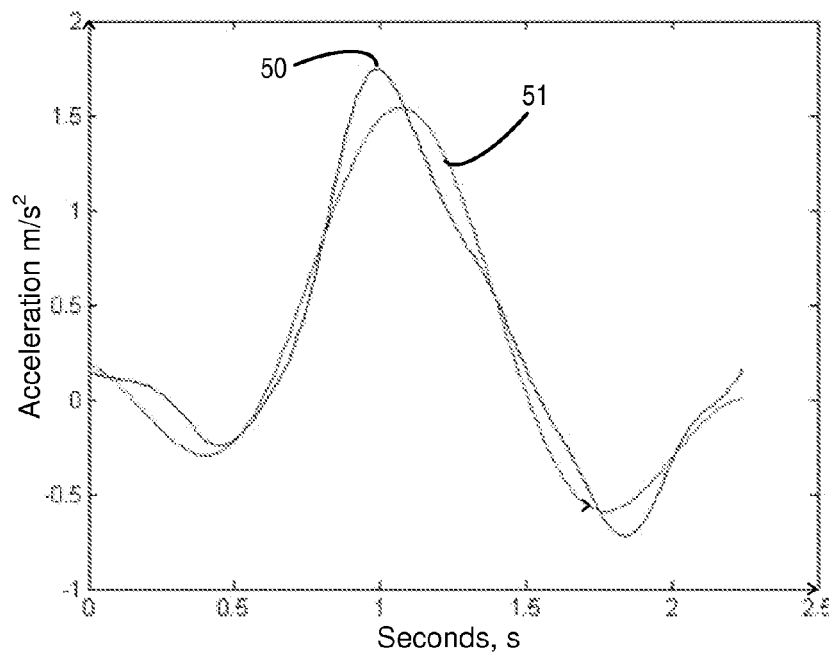
FIG. 7 illustrates an exemplary matched filter which has been optimized for use in detecting a sit-to-stand transfer.

In a preferred embodiment, the matched filter used in block 24 can be as shown in FIG. 7, which has been optimized to detect a sit-to-stand transfer. The matched filter shown in FIG. 7 excludes gravity (9.8 ms$^{-2}$) The first curve 50 shows a typical vertical acceleration pattern of a sit-to-stand transfer. The second curve 51 shows an applied matched filter characteristic that approximates the first curve 50. It will be appreciated that the matched filter characteristic may be expressed using many different functions, but in this embodiment, the matched filter characteristic is given by equation 4 below.

$$A_1 \cdot \text{sin } c[W_1(t-t_1)] + A_2 \cdot \text{sin } c[W_2(t-t_2)] \quad (4)$$

This characteristic is a combination of two sin c functions with scale parameters defined in p. p is a parameter vector with six elements:

$$[A_1, A_2, W_1, W_2, t_1, t_2] \quad (5)$$

Each entry in p defines a different scale parameter. $A_1$ and $A_2$ are amplitude scale parameters, which define the peak deviation of the two sin c waves respectively. The parameters $W_1$ and $W_2$ are frequency scale parameters, which define the frequency of the two sin c waves. The parameters $t_1$ and $t_2$ are phase scale parameters, which define the position of the sin c waves. The values of the six elements in the parameter vector p are set to tune the function of the matched filter to the sit-to-stand transfer characteristic 50 in FIG. 7.

It will be appreciated that the values of the elements of the parameter vector p can be provided by many known curve-fitting methods. In one case, the desired parameters could be calculated by applying a nonlinear least-squares regression algorithm, however many other types of fitting algorithms are well known in the art and could be applied. The nonlinear least-squares regression algorithm generates different parameter combinations corresponding to different functions. The generated functions are then fitted to the data set of desired patterns according to a least-squared error criterion. When the function yields a minimum value of least square error among the combination of parameters, an optimized fit has been found.

After matched filtering, the filtered signal is processed to identify movements that may correspond to a sit-to-stand transfer by the user. The processing consists of firstly identifying any peak having a magnitude in a predetermined range in the vert_acc_matfilt signal. In the exemplary signal shown in FIG. 6(d), peaks whose magnitudes are in the range of 110 to 200 are identified. It will be appreciated that this part of the processing can alternatively comprise identifying any peak having a magnitude above a threshold value in the vert_acc_matfilt signal. In this case, the threshold can correspond to the lower bound for the predetermined range described above. However, this classification may result in a higher false positive identification rate than the range embodiment described above.

For each identified peak, the algorithm attempts to identify respective local minima occurring within a predetermined time period before and after the identified peak in the vert_acc_matfilt signal. In the exemplary signal shown in FIG. 6(b), the algorithm looks for local minima within a period of 2 seconds before and after the identified peak. If no local minima are identified for a particular peak, that peak of the vert_acc_matfilt signal is not considered to correspond to a sit-to-stand transfer.

Finally, a candidate movement corresponding to a sit-to-stand transfer is identified as a peak having the required local minima and at which the difference between the magnitude of the peak and the magnitude of the local minimum before the peak is less than a first threshold value, the difference between the magnitude of the peak and the local minimum after the peak is less than a second threshold value, and the magnitude of the local minimum after the peak is less than the magnitude of the local minimum before the peak.

In simplified implementations of the invention, the magnitude requirements applied to the local minima can be relaxed, with the algorithm simply identifying the peak, the magnitude of the peak, and the presence of local minima before and after the peak.

In the exemplary signal shown in FIG. 6(b), the first threshold is 25 and the second threshold is 200. It will be appreciated that the values chosen for the first and second thresholds are tuned to an experimental dataset, and different threshold values could be used.

It can be seen in FIG. 6(b) that four possible movements have been highlighted as candidate sit-to-stand transfers, occurring roughly at times 1.65, 1.69, 1.78 and 1.87.

As described above with reference to step 107 of FIG. 3, candidate sit-to-stand transfers are identified as actual sit-to-stand transfers when they occur at the same time as a change in the height of the sensor unit 2 that is within a predetermined range. Thus, block 25 determines the change in height or altitude that has occurred during each candidate sit-to-stand transfer. In order for block 25 to evaluate the altitude change of a candidate sit-to-stand transfer identified in the matched filtering block 24, block 25 receives a copy of the vert_acc_matfilt signal and indications of which parts of the signal correspond to candidate sit-to-stand transfers from the matched filtering block 24. Block 25 also receives the estimated altitude measurement signal, alt_meas, from estimation block 23.

A candidate sit-to-stand transfer found in the output from the matched filter 24 consists of three key samples. These are the peak, the local minimum before the peak (min_1), and the local minimum after the peak (min_2). These samples are marked for one of the candidate sit-to-stand transfers in FIG. 6(b). In order to estimate the altitude change over the correct time period, it is necessary to identify the right samples in the altitude measurement signal.

Firstly, the nearest sample (s1) before the local minimum before the peak (min_1) whose value is larger than a threshold is found. Secondly, the nearest sample (s2) after the local minimum after the peak (min_2) whose value is larger than a threshold is found. It will be appreciated that theoretically, this threshold should be $g^2$; however in practice, different values might be provided by the training dataset due to slight inaccuracies in the accelerometer, for example. In one embodiment, this threshold is 98.

The altitude change of the candidate sit-to-stand transfer is then estimated as the difference between the altitudes at samples s1 and s2.

Preferably, since there may be small fluctuations in the altitude measurement (due to noise), the altitude change of the candidate sit-to-stand transfer is estimated as the difference between the mean of the altitude measurement over a time window starting at the second local minimum, and the mean of the altitude measurement over a time window ending at the first local minimum. These time windows can be one second, although it will be appreciated that windows of other lengths can be used. In equation form, this can be expressed as $$\text{alt\_diff} = \text{mean}(\text{alt\_meas}(s2:s2+t_w)) - \text{mean}(\text{alt\_meas}(s1-t_w:s1)) \quad (6)$$

where $t_w$ is the length of the window. In this way, the mean value of the altitude data one second before the start and one second after the candidate transfer is evaluated. When a sit-to-stand transfer has occurred, a lower altitude should be observed before the transfer (when the user 4 is in the sitting position) than the altitude observed after the transfer (when the user 4 is in the standing position).

The output of the candidate sit-to-stand transfer identification block 24 and the altitude change block 25 are provided to a decision block 26 which determines whether any of the candidates are sit-to-stand transfers. In particular, any candidate movement occurring at the same time a change in altitude or height within a predetermined range is deemed to be a sit-to-stand transfer. The change in height should be an increase in height (by definition of a sit-to-stand transfer), and the predetermined range can be, for example, between 0.1 and 0.75 meters. As described above with reference to step 107 of FIG. 3, the upper bound can be omitted at the expense of a greater false positive detection rate.

It can be seen in FIG. 6 that of the four candidate movements highlighted in FIG. 6(b), the last three occur at the same time as an increase in height that is in the range 0.1 to 0.75. Thus, the candidate movements at times 1.69, 1.78 and 1.87 are deemed to correspond to sit-to-stand transfers. The candidate movement at time 1.65 coincides with a reduction in the measured height and is therefore discarded. The algorithm then repeats for a new set of input data (represented by block 27 in FIG. 5).

As described earlier, for detected sit-to-stand transfers (block 28), the power used by the user 4 during the transfer can be estimated. This is performed in block 29. In order for the estimate to be as accurate as possible, it is necessary to determine the timing of the start and end of the sit-to-stand transfer.

Therefore, a block 30 determines the timing of the sit-to-stand transfer and receives inputs from the block 22 which estimates of the variation of the acceleration and the vertical acceleration profile after matched filtering, vert_acc_matfilt.

In a simple embodiment, s1 and s2 are used to identify the start and end of the sit-to-stand transfer for the purposes of calculating the power used.

However, as will be known to those skilled in the art, the matched filter introduces a delay which is related to the number of filter taps. This delay causes the candidate sit-to-stand transfer to be delayed with respect to the actual onset of the sit-to-stand transfer in the vert_acc_matfilt signal. Therefore, in a preferred embodiment, the output of block 22 that estimates the variation in acceleration, max_std_acc can be used to determine the actual onset of a sit-to-stand transfer.

Firstly, the most adjacent sample in the signal max_std_acc before s1 whose value is smaller than a threshold is identified. This threshold determines where the onset of the actual sit-to-stand transfer (denoted t_start) is found. In an exemplary case the threshold may be 0.35, but it will be understood that different threshold values smaller than 1 may be used, with the specific value being selected, in part, based on the size of the computing window being applied to the signal. Then, the largest local minimum of the estimate of the vertical acceleration (vert_acc) between s1 and s2 (in other words, the lowest value of vert_acc between s1 and s2) is found. The most adjacent sample after the largest local minimum of the estimate of the vertical acceleration, whose value is larger than a threshold value, which in a preferred embodiment is based on gravity (i.e. 9.8 ms$^{-2}$), is defined as the end of the actual sit-to-stand transfer (t_end). The solid black bars in FIG. 6(b) and corresponding circles in FIG. 6(a) indicate t_start and t_end for each actual sit-to-stand transfer. The values for t_start and t_end for each detected sit-to-stand transfer are provided to power calculation block 29.

Block 29 also receives the vert_acc signal from block 20 and calculates the peak power present in the sit-to-stand transfer. In particular, the section of the estimate of the vertical acceleration between the start and end of the sit-to-stand transfer (i.e. between t_start, t_end) is isolated.

As described in WO 2010/035187, the peak power during a sit-to-stand transfer can be calculated using:

$$\text{Power}(t) = m^*(\text{vert\_acc}(t)+g)^* \int_{t\_start}^{t\_end}(\text{vert\_acc}^*(t))\, dt \quad (7)$$

where m is the mass of the user 4 and g is acceleration due to gravity.

Following the computation of the power in the sit-to-stand transfer by block 29, the result is output for further processing or analysis.

It will be appreciated that the peak power output from the power computation stage 29 could be stored enabling the evaluation of the variation in power over a sustained period of time, such as one month. The evaluation could be based on sit-to-stand peak power in combination with other known parameters, such as the user's age, gender, and health conditions. The evaluation could also be performed in combination with parameters from other fall-related assessments, such as time-up-and-go. If evaluation results pass a fall-risk threshold, a caregiver or user could be alerted. Alternatively or in addition, a report could be provided for feedback on progress. Health professionals can obtain the same report for the use of providing intervention services.

There is therefore provided a method and apparatus that can identify a sit-to-stand transfer from measurements of the movement of a user. This identification subsequently allows the power used by the user in performing the movement can be calculated. In addition, in certain embodiments, the method and apparatus detect the onset and end of the transfer within a certain degree of accuracy in order for the power analysis to provide useful results.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for identifying a sit-to-stand transfer in measurements of the movement of a user, the method comprising:
    obtaining first signals corresponding to first measurements of vertical acceleration experienced by the user during movement from a first sensor that is attached to the user;
    obtaining second signals corresponding to second measurements indicating changes in height of a part of the user during movement from a second sensor that is attached to the user;
    processing the first measurements to identify candidate movements corresponding to a sit-to-stand transfer by the user by matching the first measurements to a predetermined acceleration profile for a sit-to-stand transfer to identify one or more candidate movements by identifying, for each candidate movement, a peak of the first measurements, a first local minimum in the first measurements within a predetermined time period before the identified peak and a second local minimum in the first measurements within a predetermined time period after the identified peak;
    processing the second measures to identify changes in the height of the part of the user;
    determining an identified candidate movement of the one or more candidate movements as an identified sit-to-stand transfer when the identified candidate movement coincides with an increase in the height of the part of the user;
    processing the first measurements of the identified sit-to-stand transfer to determine an estimate of power used during the identified sit-to-stand transfer;
    determining a risk of falling for the user based on the estimate of power used during the identified sit-to-stand transfer; and
    issuing an alert when the determined risk of falling exceeds a given threshold.

2. The method of claim 1, wherein the identified peak of the first measurements has a magnitude in a predetermined range.

3. The method of claim 2, wherein the candidate movement is further identified where:

the difference between the magnitude of the identified peak and a magnitude of the first local minimum is less than a first threshold value;

the difference between the magnitude of the identified peak and a magnitude of the second local minimum is less than a second threshold value; and the magnitude of the second local minimum is less than the magnitude of the first local minimum.

4. The method of claim 1, wherein determining an identified candidate movement as a sit-to-stand transfer comprises:

identifying a first sample in the second measurements that corresponds to a first time in the first measurements that is before the first local minimum;

identifying a second sample in the second measurements that corresponds to a second time in the first measurements that is after the second local minimum; and determining the change in height of the part of the user from the identified first and second samples in the second measurements.

5. The method of claim 4, wherein determining the change in height from the first and second samples comprises:

determining a first average of the height of the part of the user over an evaluation window ending with the first sample;

determining a second average of the height of the part of the user over an evaluation window beginning with the second sample; and subtracting the first average from the second average to give the change in height during the candidate sit-to-stand transfer.

6. The method of claim 1, wherein the estimate of power is based on a duration of the identified sit-to-stand transfer, and the method further comprises:

estimating a variation of the vertical acceleration; and determining at least one of a start time and an end time of the identified sit-to-stand transfer in the first measurements using the estimated variation.

7. The method of claim 6, wherein determining the start time of the identified sit-to-stand transfer comprises:

identifying a sample in the estimated variation that occurs before the first local minimum and is below a third threshold value, the sample indicating the start time of the identified sit-to-stand transfer.

8. The method of claim 6, wherein determining the end time of the identified sit-to-stand transfer comprises:

identifying a sample, s1, in the first measurements that is before the first local minimum;

identifying a sample, s2, in the first measurements that is after the second local minimum;

identifying the lowest value in the first measurements between samples s1, and s2; and identifying the end time as a time of a first sample after the lowest value in the first measurements that exceeds a fifth threshold value.

9. The method of claim 1, wherein obtaining measurements of the vertical acceleration experienced by the user during movement comprises:

obtaining three-dimensional measurements of accelerations experienced by the user during movement; and processing the three-dimensional measurements to estimate the vertical acceleration experienced by the user.

10. A non-transitory computer readable medium comprising computer program code that, when executed on a processing system, causes the processing system to identify a sit-to-stand transfer in measurements of the movement of a user by:

obtaining first measurements of the vertical acceleration experienced by the user during movement from a first sensor;

obtaining second measurements indicating changes in height of a part he user during movement from a second sensor;

processing the first measurements to identify candidate movements corresponding to a sit-to-stand transfer by the user by matching the measurements of the vertical acceleration to a predetermined acceleration profile for a sit-to-stand transfer to identify one or more candidate movements by identifying, for each candidate movement; a peak of the first measurements, a first local minimum in the first measurements within a predetermined time period before the identified peak and a second local minimum in the first measurements within a predetermined time period after the identified peak;

determining an identified candidate movement of the one or more candidate movements as an identified sit-to-stand transfer when the identified candidate movement coincides with an increase in height; and storing parameters associated with the identified candidate movement in a memory for subsequent processing to identify a risk of falling associated with the user.

11. The medium of claim 10, wherein the program causes the processing system to determine the risk of falling by:

processing the parameters associated with the identified sit-to-stand transfer to determine an estimate of power used during the identified sit-to-stand transfer;

determining the risk of falling based on the estimate of power used during the identified sit-to-stand transfer, and issuing an alert if the risk of falling exceeds a given threshold.

12. The medium of claim 11, wherein the program causes the processing system to determine a duration of the identified sit-to-stand transfer; and to estimate the power based on the duration.

13. An apparatus for identifying a sit-to-stand transfer in measurements of the movement of a user, the apparatus comprising:

a memory;

a processor that, while coupled to the memory:

receives first measurements of vertical acceleration experienced by a user during movement from a first sensor attached to the user, receives second measurements of height of a part of the user from a second sensor attached to the user, processes the first measurements to identify one or more candidate movements corresponding to a sit-to-stand transfer by the user, processes the second measurements to identify a change of the height of the part, identifies an identified candidate movement of the one or more candidate movements as an identified sit-to-stand transfer when the identified candidate movement coincides with an increase in height based on the second measurements, and stores parameters associated with the identified sit-to-stand transfer in the memory for subsequent processing to identify a risk of falling associated with the user;

wherein the processor identifies the candidate movements by matching the first measurements to a predetermined acceleration profile for a sit-to-stand transfer to identify a movement corresponding to an identified sit-to-stand transfer when the acceleration profile includes a peak, a first local minimum within a predetermined time period before the identified peak and a second local minimum within a predetermined time period after the identified peak.

14. The apparatus of claim 13, wherein the processor subsequently:
processes the parameters associated with the identified sit-to-stand transfer to determine an estimate of power used during the identified sit-to-stand transfer;
determines a risk of falling for the user based on the estimate of power used during the identified sit-to-stand transfer; and
issues an alert when the determined risk of falling exceeds a given threshold.

15. The apparatus of claim 13, wherein the identified peak of the first measurements has a magnitude in a predetermined range.

16. The apparatus of claim 15, wherein the processor identifies the identified candidate movement when, additionally:
the difference between the magnitude of the identified peak and a magnitude of the first local minimum is less than a first threshold value;
the difference between the magnitude of the identified peak and a magnitude of the second local minimum is less than a second threshold value; and
the magnitude of the second local minimum is less than the magnitude of the first local minimum.

17. The apparatus of claim 13, wherein the processor determines the change in height by:
identifying a first sample in the second measurements that corresponds to a first time in the first measurements that is before the first local minimum;
identifying a second sample in the second measurements that corresponds to a second time in the first measurements that is after the second local minimum; and
determining the change in height based on the identified first and second samples in the second measurements.

18. The apparatus of claim 17, wherein determining the change in height from the first and second samples comprises:
determining a first average of the height over an evaluation window ending with the first sample;
determining a second average of the height over an evaluation window beginning with the second sample; and
subtracting the first average from the second average to provide the change in height during the candidate sit-to-stand transfer.

19. The apparatus of claim 13, wherein the parameters associated with the identified sit-to-stand transfer includes a start time and an end time of the identified sit-to-stand transfer, and the processor estimates a variation of the first measurements to identify at least one of the start time and the end time using the estimated variation.

20. The apparatus of claim 19, wherein the processor:
identifies the start time as a sample in the estimated variation that occurs before the first local minimum and is below a third threshold value; and
identifies the end time by:
identifying a sample, s1, in the first measurements that is before the first local minimum;
identifying a sample, s2, in the first measurements that is after the second local minimum;
identifying the lowest value in the first measurements between samples s1 and s2; and
identifying the end time as a time of a first sample after the lowest value in the first measurements that exceeds a fourth threshold value.

* * * * *